United States Patent [19]
Garzia et al.

[11] 3,991,190
[45] Nov. 9, 1976

[54] TREATMENT OF VIRAL INFECTIONS

[75] Inventors: Aldo Garzia, Lodi, (Milan); Andrea Bottazzi, Lodi, both of Italy

[73] Assignee: Istituto Chemioterapico Italiano S.p.A., Italy

[22] Filed: Apr. 29, 1975

[21] Appl. No.: 572,756

[30] Foreign Application Priority Data
May 2, 1974  Italy .................................. 68367/74

[52] U.S. Cl. ................................. 424/251; 424/325
[51] Int. Cl.² ................ A61K 31/505; A61K 31/13
[58] Field of Search ............................ 424/251, 325

[56] References Cited
OTHER PUBLICATIONS
The Merck Index – Eighth Edition, (1968), p. 317.
Marcialis et al., – Chem. Abst., vol. 80, (1974), pp. 128,723g, 78721g.

*Primary Examiner*—Sam Rosen
*Attorney, Agent, or Firm*—Morton, Bernard, Brown, Roberts & Sutherland

[57] ABSTRACT

A composition of cysteamine and a compound represented by the formula

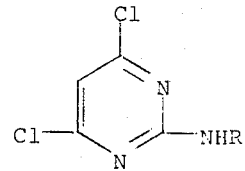

where R is hydrogen, —CHO or

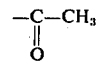

useful for the treatment of an animal infected with a virus.

21 Claims, No Drawings

TREATMENT OF VIRAL INFECTIONS

BACKGROUND OF THE INVENTION

This invention relates to the treatment of viral infections. In a particular aspect this invention relates to treatment of an animal infected with a herpes simplex virus or poliomyelitis virus, or Coxsackie or vaccinia viruses.

Infections caused by herpes simplex are painful to the host but are difficult to treat and although effective vaccines have been developed to protect an animal from poliomyelitis virus (hereinafter referred to as poliovirus), there is no known therapy for animals which do become infected.

Herpes genitalis infections, once rare, have recently become much more common in the contemporary social climate. Some authorities suspect that this virus may be the cause of some types of cancer. The infection is difficult or impossible to cure and can be passed on to infants at birth. Consequently the need for a method of treating this disease is becoming ever more important.

It is known from Experientia 29, 1442–43, 1559–1561 (1973) and 30, 1272 (1974) that 2-amino-4,6-dichloropyrimidine is effective to inhibit the growth of poliovirus in vitro by interfering with the intracellular assembly of the viral particle. It acts at the stage of capsid precursors, impairing structural protein VPO formation. This compound has proved ineffective for treating virus infections, however, because amino acids such as crysteine, cystine and glutamine, which are also present, interfere with the pyrimidine. Accordingly there exists a need for preventing this interference.

SUMMARY OF THE INVENTION

It is an object of this invention to provide a treatment of viral infections.

It is another object of this invention to provide a treatment of viral infections caused by herpes simplex virus.

It is yet another object of this invention to provide a treatment of infections caused by poliovirus.

Other objects will be apparent to those skilled in the art from the disclosure herein.

It has been discovered that a combination of pyrimidine compound represented by the formula

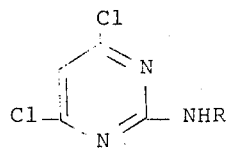

wherein R can be hydrogen, formyl $$(-\underset{\underset{O}{\|}}{C}H)$$

or acetyl

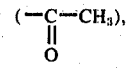

and cysteamine (2-aminoethanethiol, also known as MEA), effectively inhibits the growth of herpes simplex, Coxsackie, vaccinia and polio viruses in the presence of amino acids.

DETAILED DISCUSSION

The present invention is based on the discovery that some pyrimidine derivatives are efficaceous as inhibitors of the growth of polio virus, herpes simplex, Coxsackie $B_1$, and vaccinia viruses at dosages which have no apparent effect on the macromolecular metabolism and on the replication of uninfected cells.

The first such derivative, in the following briefly designated PY-11, is 2-amino-4,6-dichloropyrimidine, which is a compound already known and is the preferred compound. The other two derivatives, which are believed to be novel, are 2-formamido-4,6-dichloropyrimidine

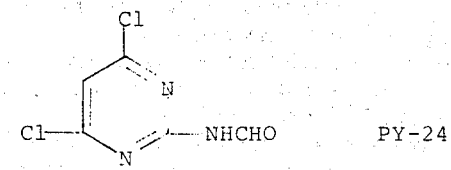

and 2-acetamido-4,6-dichloropyrimidine

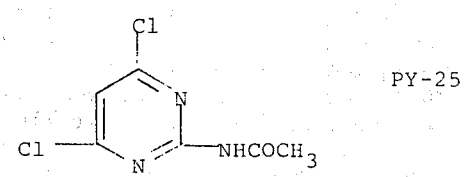

The preferred compound can be prepared by any suitable method, e.g. by the method of M. J. Langerman, J. Am. Chem. Soc. 73, 3011 (1951); a suitable method is given in example 1. The material used in the practice of this invention should be of pharmaceutically acceptable quality, free from deleterious impurities.

The formamido and acetamido derivatives can be prepared from PY-11 according to known reactions by formylation with formic acid and acetic anhydride and by acetylation with acetyl chloride, respectively, as disclosed in detail in examples 2 and 3 respectively. The materials used in the practice of this invention should be of pharmaceutically acceptable quality, free from deleterious impurities.

Cysteamine is a known compound. It can be prepared by any suitable method, many of which are known; one such method is given by D. A. Shirley, *Preparation of Organic Intermediates* (Wiley, New York, 1951) p. 189. The quality of cysteamine used in the practice of this invention should be of pharmaceutical grade, free from deleterious impurities.

It has been found by experiments in vitro that PY-11 and the other two derivatives can inhibit the growth of polio virus, especially polio 1 virus, if their concentration in the medium is sufficiently high, i.e. at a minimum effective concentration of about 30 micrograms per milliliter. However it has also been found that this activity is interfered with if certain amino acids are present in the medium; and precisely if cysteine, cystine and glutamine are present. It is to be noted that these amino acids are always present in vivo, so that in practice their interference would appear to be inevitable. The phenomena described above have also been observed with the virus herpes simplex.

It is the discovery of the present invention that the aforesaid interference can be neutralized or prevented by combining cysteamine (thioethanolamine, or briefly, MEA) with the pyrimidine. The quantity of MEA necessary for this purpose is about 2% by weight based on the weight of the pyrimidine derivative.

One object of the present invention is to furnish a procedure for treating viral infections caused by polio virus, herpes simplex, Coxsackie (especailly the $B_1$ strain) and vaccinia viruses which comprises the administration to the infected zone of at least one of the three pyrimidine derivatives described here, combined with a certain amount of cysteamine of about 1–3% based on the weight of the pyridimine compound. In particular, the preferred quantity is about 2% based on the weight of the pyridimine compound.

Tests in vivo carried out on rabbits having herpetic keratitis and treated with an ointment containing PY-11 and 2% of cysteamine have confirmed the utility of this invention. A formulation suitable for treating a herpes simplex infection consists in an ointment containing about 0.4% of the indicated derivative and 0.008% of cysteamine. In general, any pharmaceutically acceptable ointment, cream or lotion can be used to formulate the combination of this invention. Many such preparations are known and are well within the skill of the pharmaceutical formulator.

For the treatment of systemic viral infections such as those caused by polio, Coxsackie, and vaccinia viruses, the combination of the present invention is administered orally in a suitable pharmaceutically acceptable carrier. The combination is administered in an amount sufficient to provide a growth-inhibiting blood concentration of at least 30 $\mu$g/ml or more, for example, 30 to 250 $\mu$g/ml.

The invention will be better understood with reference to the following examples. It is understood, however, that the examples are intended for illustration only, and it is not intended that the invention be limited thereby.

EXAMPLE 1

2-Amino-4,6-Dichloropyrimidine

2-Amino-4,6-dichloropyrimidine was prepared according to a modification of the method of M. J. Langerman, J. Am. Chem. Soc. 73, 3011 (1951). To a reaction vessel fitted with a reflux condenser and a heat source there was delivered 2-amino-4,6-dihydroxypyrimidine 1.27 g (0.1 mole), phosphorous oxychloride 13.0 g (0.9 mole) and dimethylaniline 3.6 g (0.3 mole). These ingredients were mixed by swirling and then heated to reflux at about 107° C for about 8 hours.

The excess phosphorous oxychloride was removed by evaporation and the thick, molten residue was poured carefully into 80 ml of hot water (at about 80° C) with agitation thereby obtaining a suspension. Sufficient concentrated sodium hydroxide solution was added to render the suspension definitely basic, e.g. pH 8–9 or more. The mixture was then filtered and the filter cake was washed with water until the washings were neutral. The product was recrystallized from benzene. There was obtained 2-amino-4,6-dichloropyrimidine (PY-11) having a melting point of 221° C, yield 70%.

PY-11 was formulated into a collyrium using the following formula:

| | |
|---|---|
| PY-11 | 0.4 g |
| Cysteamine . HCl | 0.008 |
| Sodium carboxymethyl cellulose | 0.5 |
| Propylene glycol | 28.0 |

Bidistilled water, quantity sufficient to make 100 ml. This lotion was administered daily, 2 drops per eye, to human patients suffering from herpes keratitis until the keratitis cleared.

PY-11 was formulated in a colloidal gel using the following formula:

| | |
|---|---|
| PY-11 | 0.4 g |
| Cysteamine . HCl | 0.008 |
| Sodium carboxymethyl cellulose | 2.0 |
| Propylene glycol | 28.0 |

Bidistilled water, quantity sufficient to make 100 ml. This gel was applied topically on a daily basis to humans suffering from herpes genitalis infections until the lesions disappeared.

PY-11, in amino-acid free media, greatly reduced the growth of polio 1 and Coxsackie $B_1$ viruses, but when l-cysteine and l-glutamine were added to the media, the anti-viral action was less evident. However when cysteamine was added to the media, the anti-viral action of PY-11 was fully restored. Similar results have been obtained with vaccinia and herpes simplex viruses.

Further experiments have shown that PY-11 prevented the growth of polio virus 1 if added to the cultures within 2 hours after inoculation. It had no apparent effect either on the wet synthesis of infectious virus RNA or on the virus-induced damage to the cell. The action of PY-11 seemed to be limited to the impairment of the assembly of capsid precursors thereby preventing the production of infectious particles.

With vaccinia virus, PY-11 could be added as late as 7-8 hours after inoculation and still prevent virus growth at a time when the synthesis of virus DNA and early proteins has been completed and cells are undergoing cytopathic effect.

The anti-viral activity is given in the following table:

| Anti-Viral Activity in Culture Medium | | | |
|---|---|---|---|
| | PY-11 | PY-24 | PY-25 |
| Maximum non-cytotic concentration $\mu$g/ml | 250 | 10 | 10 |
| Anti-viral activity* against polio 1 | 99% | 90% | 85% |
| Coxsackie $B_1$ | 99 | 90 | 80 |
| Vaccinia | 90 | 90 | 90 |
| Herpes simplex | 90 | 85 | 85 |

*Inhibition of virus growth at 24 hours.

EXAMPLE 2

2-Formamido-4,6-Dichloropyrimidine

A 250 ml. three necked flask was fitted with a mechanical stirrer, a thermometer, and a reflux condenser with drying tube. To the flask was charged 70 ml. of a 98% formic acid and 3.85 g (0.025 mole) of 2-amino-4,6-dichloropyrimidine as prepared in example 1. Acetic anhydride, 30 ml. was added slowly with stirring to maintain temperature below 50° C. When the addition of acetic anhydride was complete, the mixture was heated for 6 more hours at 50° C and then allowed to stand overnight at room temperature. Excess formic acid and acetic anhydride were evaporated under vacuum. The solid residue was crystallized from 15 ml. of ethyl alcohol. There was obtained 3.7 g of 2-formamido-4,6-dichloropyrimidine (PY-24) in the form of white crystals, melting point, 142°–144° C, yield 77%.

Analysis

Calculated for $C_5H_3Cl_2N_3O$: C, 31.28%; H, 1.57%; Cl, 36.93%; N, 21.89%; O, 8.33%.

Found: C, 31.20%; H, 1.60%; Cl, 36.98%; N, 21.92%; O, 8.30%.

PY-24 was tested for inhibition of virus growth against polio 1 virus, Coxsackie $B_1$, herpes simplex and vaccinia viruses as described in example 1. It was highly effective and cysteamine prevented interference from amino acids.

The anti-viral activity is given in the table in example 1.

EXAMPLE 3

2-Acetamido-4,6-Dichloropyrimidine

A 250 ml. three necked flask was fitted with a mechanical stirrer and a reflux condenser with drying tube. The flask is charged with 50 ml. of acetic anhydride and 3.85 g of 2-amino-4,6-dichloropyrimidine (0.025 mole). Then, 10 ml. of acetyl chloride was added slowly and the mixture was heated to 110° C for 8 hours. The mixture was allowed to stand overnight at room temperature. The crystalline solid product which formed was filtered and washed with water and sodium bicarbonate solution. It was then recrystallized from 50% alcohol. There was obtained 3.8 g of 2-acetamido-4,6-dichloropyrimidine (PY-25) in the form of white crystals, melting point, 198°–200° C, yield, 74.5%.

Analysis

Calculated for $C_6H_5Cl_2N_3O$: C, 34.98%; H, 2.45%; Cl, 34.42%; N, 20.39%; O, 7.76%.

Found: C, 34.88%; H, 2.50%; Cl, 34.47%; N, 20.44%; O, 7.71%.

PY-25 was tested for inhibition of virus growth against polio 1 virus, Coxsackie $B_1$, herpes simplex and vaccinia viruses as described in example 1. It was highly effective and cysteamine prevented interference from amino acids.

The anti-viral activity is given in the table in example 1.

We claim:

1. A composition suitable for treating an animal infected with herpes simplex virus, poliomyelitis virus, Coxsackie virus, or vaccinia virus comprising an effective amount to treat the infection when administered to the animal of a combination consisting essentially of a pyrimidine compound of the formula

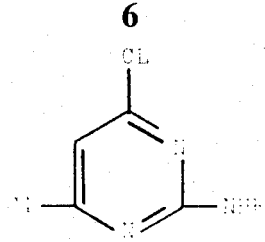

wherein R is hydrogen,

or

and cysteamine.

2. A method for treating an animal infected with herpes simplex virus, poliomyelitis virus, Coxsackie virus, or vaccinia virus comprising administering to the animal an effective amount to treat the infection of the composition of claim 1.

3. The method of claim 2 wherein the cysteamine is in an amount of about 1 to 3 weight percent of the pyrimidine compound.

4. The method of claim 3 wherein the pyrimidine compound is orally administered in an amount sufficient to provide a blood pyrimidine concentration of at least 30 micrograms per milliliter.

5. The method of claim 4 wherein the animal is infected by poliomyelitis virus and R is hydrogen.

6. The method of claim 4 wherein the animal is infected by Coxsackie virus and R is hydrogen.

7. The method of claim 4 wherein the animal is infected by vaccinia virus and R is hydrogen.

8. The composition of claim 1 wherein the cysteamine is present in an amount of about 1–3% based on the weight of the pyrimidine compound.

9. The composition of claim 8 wherein the cysteamine is present in an amount of about 2% based on the weight of the pyrimidine compound.

10. The composition of claim 1 wherein R of the pyrimidine is hydrogen.

11. The composition of claim 1 wherein R of the pyrimidine is

12. The composition of claim 1 wherein R of the pyrimidine is

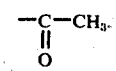

13. A method of treating an animal requiring treatment for an infection caused by herpes simplex virus by applying to said infection an effective amount of the composition of claim 1 to treat the infection wherein cysteamine is in an amount of about 2% based on the weight of the pyrimidine compound.

14. The method of claim 13 wherein the composition contains a pharmaceutically acceptable carrier at a concentration of about 0.4% of the pyrimidine compound and 0.008% of cysteamine.

15. The method of claim 13 wherein said pyrimidine compound is 2-amino-4,6-dichloropyrimidine.

16. The method of claim 13 wherein said pyrimidine is 2-formamido-4,6-dichloropyrimidine.

17. The method of claim 13 wherein said pyrimidine is 2-acetamido-4,6-dichloropyrimidine.

18. A method of treating an animal requiring treatment for an infection caused by polio virus by administering to said animal 2-amino-4,6-dichloropyrimidine and cysteamine in an amount sufficient to provide a blood 2-amino-4,6-dichloropyrimidine concentration between 30 and 250 µg/ml.

19. A method of treating an animal requiring treatment for an infection caused by Coxsackie virus by administering to said animal 2-amino-4,6-dichloropyrimidine and cysteamine in an amount sufficient to provide a blood 2-amino-4,6-dichloropyrimidine concentration between 30 and 250 µg/ml.

20. A method of treating an animal requiring treatment for an infection caused by vaccinia virus by administering to said animal 2-amino-4,6-dichloropyrimidine and cysteamine in an amount sufficient to provide a blood 2-amino-4,6-dichloropyrimidine concentration between 30 and 250 µg/ml.

21. A composition suitable for treating an animal infected with herpes simplex virus, poliomyelitis virus, Coxsackie virus, or vaccinia virus comprising an effective amount of a pyrimidine compound of the formula

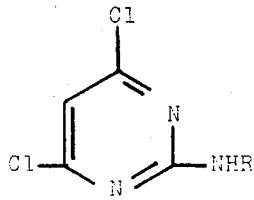

wherein R is hydrogen,

or

to treat the infection when administered to the animal and a sufficient amount of cysteamine to inhibit the interference on the activity of the pyrimidine compound by cysteine, cystine or glutamine.

* * * * *